(12) United States Patent
Ikemoto et al.

(10) Patent No.: US 8,969,563 B2
(45) Date of Patent: Mar. 3, 2015

(54) CALCIUM SALT OF PYRROLOQUINOLINE QUINONE

(75) Inventors: Kazuto Ikemoto, Niigata (JP); Masahiko Nakano, Tokyo (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 0 days.

(21) Appl. No.: 13/825,228

(22) PCT Filed: Sep. 22, 2011

(86) PCT No.: PCT/JP2011/071697
§ 371 (c)(1),
(2), (4) Date: May 9, 2013

(87) PCT Pub. No.: WO2012/039474
PCT Pub. Date: Mar. 29, 2012

(65) Prior Publication Data
US 2013/0225632 A1    Aug. 29, 2013

(30) Foreign Application Priority Data
Sep. 22, 2010    (JP) .................................. 2010-211883

(51) Int. Cl.
*C07D 471/04*    (2006.01)
(52) U.S. Cl.
CPC .................................. *C07D 471/04* (2013.01)
USPC ............................................. 546/84; 514/292
(58) Field of Classification Search
USPC ............................................. 514/292; 546/84
See application file for complete search history.

(56) References Cited

U.S. PATENT DOCUMENTS

2010/0261749 A1*    10/2010    Kamimura et al. ........... 514/292

FOREIGN PATENT DOCUMENTS

| JP | 62 246575 | 10/1987 |
| JP | 2 53477 | 2/1990 |
| JP | 3 112912 | 5/1991 |
| JP | 7 113024 | 5/1995 |
| JP | 2751183 | 2/1998 |

OTHER PUBLICATIONS

Williams; Acta Cryst., 2005, D61, 75-79.*
Afolabi; Biochemistry 2001, 40, 9799-9809.*
Berge, S. et al., "Pharmaceutical Salts," Journal of Pharmaceutical Sciences, vol. 66, No. 1, pp. 1 to 19, table I (Jan. 1977).
"A new redox-cofactor vitamin for mammals," Brief communications, Nature Publishing Group, vol. 422, p. 832, (Apr. 24, 2003).
Corey, E.J. et al., "Total Synthesis of the Quinonoid Alcohol Dehydrogenase Coenzyme (1) of Methylotrophic Bacteria," Journal American Chemical Society, vol. 103, p. 5599 to 5600, (1981).
International Search Report Issued Dec. 13, 2011 in PCT/JP11/71697 Filed Sep. 22, 2011.

* cited by examiner

*Primary Examiner* — John Mabry
*Assistant Examiner* — Daniel Carcanague
(74) *Attorney, Agent, or Firm* — Oblon, McClelland, Maier & Neustadt, L.L.P.

(57) ABSTRACT

An object of the present invention is to provide an industrially useful method for producing a calcium salt of pyrroloquinoline quinone, without using large amounts of organic solvents, and highly pure crystals produced thereby. According to the present invention, a highly pure calcium salt of pyrroloquinoline quinone can be produced by reacting an alkali metal salt of pyrroloquinoline quinone with a source of calcium ions.

6 Claims, 6 Drawing Sheets

CALCIUM SALT OF PYRROLOQUINOLINE QUINONE

CROSS-REFERENCE TO RELATED APPLICATION

This application enjoys the benefit of Japanese Patent Application No. 2010-211883, filed on Sep. 22, 2010. The disclosure of this earlier application is incorporated herein by reference in its entirety.

TECHNICAL FIELD

The present invention relates to a method for producing a calcium salt of pyrroloquinoline quinone and to a calcium salt of pyrroloquinoline quinone obtained by the method. The present invention also relates to use of the calcium salt of pyrroloquinoline quinone.

BACKGROUND ART

Pyrroloquinoline quinone (hereinafter sometimes referred to as "PQQ") has been proposed as a possible new vitamin (see, for example, Non-patent document 1), and has attracted much attention as a useful material for dietary supplements, cosmetics, etc. Moreover, PQQ is present not only in bacteria but also in eukaryotic molds and yeasts and plays an important role as a cofactor. Also, PQQ has been found to have many physiological activities such as cell growth-promoting activity, anti-cataract activity, hepatic disease-preventing and therapeutic activity, wound healing activity, antiallergic activity, reverse transcriptase-inhibiting activity and glyoxalase I-inhibiting activity—anticancer activity, nerve fiber regeneration, and the like. It is known in the art that the higher crystallinity provides the chemical stability and the longer shelf life, and consequently an agent having such higher crystallinity is less in need of stabilizing, has a longer shelf life, and has the potential to be provided in the form of relatively simple packaging.

PQQ can be obtained by subjecting PQQ obtained by methodologies such as organic chemical syntheses (Non-patent document 2) or fermentation processes (Patent document 1) to chromatography, concentrating the PQQ fraction in the effluent and adding an organic solvent to the fraction to crystallize PQQ by crystallization (Patent document 2), followed by drying the crystallized PQQ. An alkali metal salt of PQQ may be obtained by precipitation from the corresponding aqueous solution by adding an alcohol to the solution to reduce the solubility of the salt. The alkali metal salt, however, does not have high crystallinity. In addition, this method involves using an organic solvent that is expensive, flammable and costly in terms of waste disposal. Thus, a method without using such solvent is sought after. Also, in Non-patent document 2, a method for producing the disodium salt of PQQ in crystal form is provided, but this method has low productivity and is not industrially useful. Moreover, calcium ions are important as nutritional components and desirably ingested simultaneously with pyrroloquinoline. Any specific method for producing a calcium salt of PQQ, however, has not been reported so far.

Although an alkaline-earth metal salt of PQQ as well as an alkaline metal salt of PQQ is disclosed in Patent document 2, there is no working example of such an alkaline-earth metal salt. Moreover, this method involves crystallization by using an organic solvent, resulting in costly facilities for handling flammable substances and waste water. Moreover, alkali metal salts of PQQ are soluble in water, and readily react with amine, carbonyl and reducing compounds, in particular in such a moisture-containing environment where these salts are dissolved. The alkali metal salts are therefore required to have a low solubility in water in order to increase their stability. It is desired that PQQ is readily absorbed when administered as food or drugs.

Furthermore, PQQ and salts thereof are often obtained in red or dark red color. These colors are known to be unique to PQQ, and heightened when PQQ is mixed with food or drugs, which may result in failure to adjust the color of the mixture to an intended target color. In particular, the color of PQQ may present a difficulty in designing a target color in food products in which palatability is important. Therefore, the color of PQQ is desirably close to white. The color of PQQ may look white by coating or mixing with other components. However, addition of non-essential components has a disadvantage of a decreased level of freedom in designing the ingredients of food or drugs. Also, in the case of coating, the coated PQQ is required to have the same functionalities as the original PQQ or to return to the original PQQ. Alternatively, it is envisaged that the color is changed by chemical modification through organic synthesis, which needs many organic solvents and highly toxic reagents.

In addition, since PQQ is highly reactive, it is desirably in the form of solid in the place where it comes in contact with food, and of liquid in the intestines where it is absorbed.

PRIOR ART DOCUMENTS

Patent Document

[Patent document 1] Japanese Patent No. 2751183
[Patent document 2] Japanese Examined Patent Application Publication No. 07-113024

Non-Patent Document

[Non-patent document 1] Nature, vol. 422, 24, April, 2003, p. 832 [Non-patent document 2] JACS, vol. 103, pp. 5599-5600 (1981)

SUMMARY OF THE INVENTION

Problem to be Solved by the Invention

The present inventors have found that a calcium salt of pyrroloquinoline quinone can be produced by precipitation from a solution obtained by mixing an aqueous solution of pyrroloquinoline quinone or an alkali metal salt thereof with an aqueous solution of a source of calcium ions, and that the calcium salt thus obtained has high crystallinity and a low solubility in water. The present inventors have also found that a white calcium salt is obtained under predetermined conditions. The present invention is based on these findings.

An object of the present invention is to provide a method for producing a salt of PQQ which has high crystallinity as well as a low solubility in water, and readily releases PQQ, without using large amounts of organic solvents. Specifically, an object of the present invention is to provide a method for producing a calcium salt of PQQ and highly pure crystals produced thereby.

Means for Solving Problem

According to the present invention, the following inventions are provided:

(1) a calcium salt of pyrroloquinoline quinone, having a molar ratio of the pyrroloquinoline quinone ions to the calcium ions of 1:0.5 to 1.5;
(2) the calcium salt of pyrroloquinoline quinone according to (1), which is obtained by precipitation from a mixture obtained by mixing pyrroloquinoline quinone or an alkali metal salt thereof with a source of calcium ions in a solution;
(3) the calcium salt of pyrroloquinoline quinone according to (2), wherein the source of calcium ions is selected from the group consisting of calcium carbonate, calcium chloride, and calcium hydroxide;
(4) the calcium salt of pyrroloquinoline quinone according to any of (1) to (3), which is being white in color;
(5) a crystal of the calcium salt of pyrroloquinoline quinone according to any of (1) to (4);
(6) the crystal of the calcium salt of pyrroloquinoline quinone according to (6), which is exhibiting peaks in 2θ at 7.7°, 10.6°, 19.1°, 26.4°, and 38.6° (each within ±0.4°) in the powder X-ray diffraction using Cu Kα radiation;
(7) the crystal of the calcium salt of pyrroloquinoline quinone according to (5), which is exhibiting peaks in 2θ at 9.8°, 15.3°, 17.1°, 19.7°, 26.3°, and 28.3° (each within ±0.4°) in the powder X-ray diffraction using Cu Kα radiation;
(8) the crystal of the calcium salt of pyrroloquinoline quinone according to (5), which is exhibiting peaks in 2θ at 8.8°, 17.5°, 25.4°, 28.1°, 30.5°, and 33.9° (each within ±0.4°) in the powder X-ray diffraction using Cu Kα radiation;
(9) a pyrroloquinoline quinone-containing composition comprising the calcium salt of pyrroloquinoline quinone according to any of (1) to (4) or the crystal of the calcium salt of pyrroloquinoline quinone according to any of (5) to (8), and a chelating substance;
(10) the composition according to (9), wherein the chelating substance is one or more selected from the group consisting of phosphoric acids, pyrophosphoric acid, nucleic acids, phytic acid, tartaric acid, succinic acid, citric acid, EDTA, hexametaphosphoric acid and polyphosphoric acids;
(11) a method for producing a calcium salt of pyrroloquinoline quinone, comprising obtaining a precipitate from a mixture obtained by mixing pyrroloquinoline quinone or an alkali metal salt thereof with a source of calcium ions in a solution;
(12) the method according to (11), wherein water is present in the mixture;
(13) the method according to (11) or (12), wherein the mixture has a pH of less than 4;
(14) The method according to any of (11) to (13), wherein the source of calcium ions is selected from the group consisting of calcium carbonate, calcium chloride, and calcium hydroxide;
(15) a calcium salt of pyrroloquinoline quinone, which is produced by the method according to any of (11) to (14);
(16) a crystal of a calcium salt of pyrroloquinoline quinone, which is exhibiting peaks in 2θ at 7.7°, 10.6°, 19.1°, 26.4°, and 38.6° (each within ±0.4°) in the powder X-ray diffraction using Cu Kα radiation;
(17) a crystal of a calcium salt of pyrroloquinoline quinone, which is exhibiting peaks in 2θ at 9.8°, 15.3°, 17.1°, 19.7°, 26.3°, and 28.3° (each within ±0.4°) in the powder X-ray diffraction using Cu Kα radiation;
(18) a crystal of a calcium salt of pyrroloquinoline quinone, which is exhibiting peaks in 2θ at 8.8°, 17.5°, 25.4°, 28.1°, 30.5°, and 33.9° (each within ±0.4°) in the powder X-ray diffraction using Cu Kα radiation.

The present invention is advantageous in that a stable calcium salt of PQQ which has a low solubility in water and high crystallinity can be produced with a high purity by an industrially useful method without using any organic solvent. Also, it is advantageous in that the calcium salt of PQQ obtained can be in solution at time of use, and thus has a high absorbability. It is also advantageous in that the calcium salt of a white or near-white (pale red) color of PQQ can be produced.

DETAILED DESCRIPTION OF THE INVENTION

According to the present invention, a calcium salt of pyrroloquinoline quinone can be produced by mixing pyrroloquinoline quinone or an alkali metal salt thereof with a source of calcium ions in a solution.

The pyrroloquinoline quinone used in the present invention has the structure represented by the formula (1).

[Compound 1]

(1)

The term "alkali metal salt of pyrroloquinoline quinone" as used herein refers to an alkali metal salt of the compound represented by formula (1).

The term "calcium salt of pyrroloquinoline quinone" as used herein refers to a calcium salt of the compound represented by formula (1). The calcium salt of pyrroloquinoline quinone includes any hydrate thereof.

The term "a crystal of a calcium salt of pyrroloquinoline quinone" as used herein refers to a crystal of a calcium salt of the compound represented by formula (1), which are in the state where pyrroloquinoline quinone molecules are regularly arranged in the solid state and generally are highly pure and highly stable. Whether or not the calcium salt of pyrroloquinoline quinone is in a crystalline form can be determined by detecting peaks in the X-ray powder diffraction.

The diffraction angle 2θ by powder X-ray diffraction can be measured under the following conditions.
(Measurement Conditions)
Instrument: RINT 2500 from Rigaku Corporation
X-ray: Cu/Tube voltage 40 kV/Tube current 100 mA
Scanning Rate: 4.000°/min
Sampling Width: 0.020°

Besides, a common powder X-ray diffraction instrument equipped with a monochromator can measure the diffraction angle.

The alkali metal salt of pyrroloquinoline quinone used in the present invention includes salts of sodium, potassium, lithium, cesium, rubidium, and the like. Preferred are sodium and potassium salts, and particularly preferred is sodium salt, which is readily available. These salts may be used singly or in combination thereof. Pyrroloquinoline quinone may be substituted with one to three alkali metals to form an alkali metal salt thereof, which may be any of a monoalkali metal salt, a dialkali metal salt and a trialkali metal salt, and preferably a dialkali metal salt. The alkali metal salt of pyrroloquinoline quinone is particularly preferably a disodium salt.

The alkali metal salt of PQQ used in the present invention may be commercially available. Also, the salt can be produced by organic chemical syntheses and fermentation processes. The salt of pyrroloquinoline quinone used as a raw material may be crystalline or amorphous. Moreover, it may contain some impurities.

Pyrroloquinoline quinone or an alkali metal salt thereof used in the present invention can be used in solution. Any solvent that allows the reaction to proceed may be used. Pyrroloquinoline quinone or an alkali metal salt thereof can be dissolved in a solvent such as water, alcohol, dimethyl sulfoxide, dimethylformamide, dimethylacetamide, and N-methyl pyrrolidone to form a solution. The solvent may be used singly or in combination with one or more other solvents. Preferred is water as the solvent used, i.e., an aqueous solution.

The solution of pyrroloquinoline quinone or an alkali metal salt thereof preferably has a concentration of, for example, 0.1 to 100 g/L, and more preferably of 1 to 20 g/L.

The pH of the solution of pyrroloquinoline quinone or an alkali metal salt thereof is eventually adjusted to preferably 1 to 12, more preferably 2 to 9, and even more preferably 2 to 7. Moreover, the number of calcium substitutions in the calcium salt can be controlled by adjusting and selecting the pH value. The salts having the number of calcium substitutions of 1 and 1.5 per PQQ can be obtained by adjusting the pH of the solution to 2 to 4 (preferably 2.5 to 4) and to more (for example, more than 4 and 7 or less, and preferably 4.5 to 7), respectively. As described below, if a white calcium salt of PQQ is produced, then the pH here can be adjusted to less than 4 (for example, 1.5 or more and less than 4, preferably 1.5 to 3.5, and more preferably 2 to 3).

In the addition procedure for adjusting the pH, an acid or alkali can be added to a solution of PQQ or an alkali metal salt thereof to adjust the pH of the solution. Any kind of acid or alkali that is poorly reactive with pyrroloquinoline quinone and calcium is preferably used for adjusting the pH of the solution. The acid or alkali may be inorganic or organic. Inorganic acids include, for example, hydrochloric acid, hydrogen bromide, hydrogen iodide, perchloric acid, sulfuric acid, phosphoric acid and nitric acid, and organic acids include, for example, acetic acid, formic acid, oxalic acid, lactic acid and citric acid. Inorganic alkalis include, for example, sodium hydroxide, potassium hydroxide, sodium carbonate, potassium carbonate, calcium carbonate, calcium bicarbonate and calcium oxide, and organic alkalis include, for example, quaternary ammonium hydroxide such as tetramethylammonium hydroxide and amines. These may be used singly or in combination thereof.

The operation of adjusting the pH of the solution in the present invention is performed at any temperature, and generally convenient is a temperature of −20° C. to 140° C., preferably 0 to 140° C., and more preferably 20 to 90° C. It is more convenient to increase the solubility of an alkali metal salt of pyrroloquinoline quinone in a solvent by warming the solution. However, as described below, a white calcium salt of PQQ is preferably produced at a temperature of 38° C. or less, and more preferably of −20° C. to 30° C. The lower temperature can yield a precursor that turns white more easily.

As a source of calcium ions used in the present invention, any substance that can provide calcium ions may be used, including calcium compounds such as, for example, calcium chloride, calcium bromide, calcium iodide, calcium carbonate, calcium bicarbonate, calcium hydroxide, calcium acetate, calcium oxide, calcium lactate, and calcium phosphate. The source of calcium ions used in the present invention is a substance preferably having a solubility at 25° C. of 0.01 g/L or more and more preferably of 1 g/L or more. From the viewpoint of solubility, preferred are calcium carbonate, calcium chloride, and calcium hydroxide, and more preferred is calcium chloride.

The source of calcium ions used in the present invention can be used as is (as powder) or in solution, preferably in solution. Any solvent that allows the reaction to proceed may be used and the source of calcium ions can thus be used by dissolving in solvents such as water, alcohol, dimethyl sulfoxide, dimethylformamide, and dimethylacetamide. The solvent may be used singly or in combination with one or more other solvents. Preferred is water as the solvent used, i.e., an aqueous solution.

A weight ratio of pyrroloquinoline quinone or an alkali metal salt thereof to a source of calcium ions can be 1:0.1 to 100, preferably 1:0.1 to 20, more preferably 1:0.1 to 10, and further preferably 1:0.3 to 5.

According to the present invention, a calcium product can be produced by reacting pyrroloquinoline quinone or an alkali metal salt thereof with a source of calcium ions followed by precipitation.

That is, pyrroloquinoline quinone or an alkali metal salt thereof can be mixed with a source of calcium ions in a solution to form a calcium salt of PQQ, which is then subjected to precipitation to obtain the calcium product.

The step of "mixing pyrroloquinoline quinone or an alkali metal salt thereof with a source of calcium ions in a solution" as used herein may involve reacting pyrroloquinoline quinone or an alkali metal salt thereof with calcium ions in a solvent, for example, by mixing a solution of pyrroloquinoline quinone or an alkali metal salt thereof with a solution of a source of calcium ions, or adding a source of calcium ions to a solution of pyrroloquinoline quinone or an alkali metal salt thereof.

"Mixing" as used herein can be accomplished by adding one object to be mixed to the other object to be mixed, or adding the objects to be mixed to a separate vessel.

For "adding" as used herein, an additive may be added at once or gradually to an object to which the additive is to be added.

In the method according to the present invention, the reaction pH is not specifically limited, but can be set, for example, in a range of 1 to 12, preferably 2 to 9, and more preferably of 2 to 7. Alternatively, the reaction pH may be less than 4, preferably 1.5 or more and less than 4, more preferably 1.5 to 3.5, and further preferably 2 to 3.

In the method according to the present invention, the reaction temperature is not specifically limited, but can be set, for example, in a range of −20 to 140° C., and preferably 0 to 120° C.

In the method according to the present invention, the reaction time is not specifically limited, but can be set, for example, in a range of 5 minutes to 1 week.

A (red) calcium salt of PQQ according to the present invention produced through the above-mentioned reaction has preferably the ratio of pyrroloquinoline quinone ions to calcium ions of 1:0.5 to 1.5, and more preferably 1:1 to 1.5. The above ratio indicates that a salt is formed between the carboxylic group of PQQ and calcium ion. Moreover, highly crystalline substances often have greater stability, and also the present invention is preferably crystalline.

The operation procedures will now be described in detail.

PQQ or an alkali metal salt thereof is dissolved in water. Even though it is not completely dissolved, the reaction can proceed. An acid or alkali may be added for adjusting the pH of the solution. PQQ or an alkali metal salt thereof here is desirably present at a concentration of 0.1 to 100 g/L, and more desirably 1 to 20 g/L. The temperature of the solution here may be set at 0 to 140° C. Preferably, the solution at a temperature of 20 to 90° C. is easily used without using any special equipment. Since the solubility tends to increase with temperature, the solution at a temperature of 50° C. or more improves productivity. Addition of calcium chloride to the solution here can precipitate the calcium salt of PQQ. Calcium can be added in the form of an aqueous solution or a powder. The mixing time is not specifically limited, but can be set in a range of five minutes to about one week. Only a short time is required on a small scale, while a longer time on a large scale.

Moreover, a calcium salt of PQQ can be obtained as a white product in the present invention. The white calcium salt of PQQ according to the present invention can be formed via a (red) calcium salt of PQQ obtained as described above.

The white calcium salt of PQQ according to the present invention is (a precipitate) obtained by precipitating from a mixture obtained by mixing pyrroloquinoline quinone or an alkali metal salt thereof with a source of calcium ions in a solution. That is, the white calcium salt of PQQ can be obtained by allowing the red calcium salt of PQQ to stand in a water-containing environment at a predetermined pH for a definite period of time.

The phrase "stand in a water-containing environment" as used herein means that in a production system, a red calcium salt of PQQ contained in the mixture of pyrroloquinoline quinone or an alkali metal salt thereof and a source of calcium ions are brought into contact with water. For example, the red calcium salt of PQQ may be present in an aqueous solution or a mixed solution of water and an organic solvent. Preferably, the red calcium salt of PQQ is present in an aqueous solution.

A mixture obtained by mixing pyrroloquinoline quinone or an alkali metal salt thereof with a source of calcium ions in a solution can be adjusted to have a pH of less than 4, preferably 1.5 or more and less than 4, more preferably 1.5 to 3.5, further preferably 2 to 3. If the mixture obtained by mixing pyrroloquinoline quinone or an alkali metal salt thereof with a source of calcium ions in a solution has a pH of less than 4, then the mixture can be used as it is without any special adjustment.

In the addition procedure for adjusting the pH, an acid or alkali can be added to the mixture to adjust the pH of the mixture. Any kind of acid or alkali is used to adjust the pH of the mixture. The acid or alkali may be inorganic or organic. Inorganic acids include, for example, hydrochloric acid, hydrogen bromide, hydrogen iodide, perchloric acid, sulfuric acid, phosphoric acid and nitric acid, and organic acids include, for example, acetic acid, formic acid, oxalic acid, lactic acid and citric acid. Inorganic alkalis include, for example, sodium hydroxide, potassium hydroxide, sodium carbonate, potassium carbonate, calcium carbonate, calcium bicarbonate and calcium oxide, and organic alkalis include, for example, quaternary ammonium hydroxide such as tetramethylammonium hydroxide, and amines. These may be used singly or in combination thereof.

The mixture obtained by mixing pyrroloquinoline quinone or an alkali metal salt thereof with a source of calcium ions in a solution can be allowed to stand in a water-containing environment for two hours or more, preferably 24 hours or more, more preferably 48 hours or more, and further preferably 72 hours or more.

The mixture obtained by mixing pyrroloquinoline quinone or an alkali metal salt thereof with a source of calcium ions in a solution may be stirred. The stirring can be performed by subjecting the mixture to magnetic stirring, mechanical stirring, manual stirring, shake stirring, etc.

The reaction of the mixture obtained by mixing pyrroloquinoline quinone or an alkali metal salt thereof with a source of calcium ions in a solution can be carried out at a temperature of −20 to 120° C., and more preferably 0 to 80° C. In the reaction in which the reaction product turns white, the higher the reaction temperature is, the larger the reaction rate becomes.

For producing a white calcium salt of pyrroloquinoline quinone, the following steps, for example, can be carried out:

(i) mixing an aqueous solution of pyrroloquinoline quinone or an alkali metal salt thereof with an aqueous solution of a source of calcium ions;

(ii) obtaining a precipitate from the mixture obtained in the step (i); and (iii) allowing the mixture containing the precipitate obtained in the step (ii) to stand at a pH of less than 4 for two hours or more.

Preferably, the (white) calcium salt of PQQ produced through the steps above has a ratio of pyrroloquinoline quinone ions to calcium ions of 1:0.5 to 1.5, and more preferably 1:1 to 1.5.

The precipitated solid is separated from the liquid through filtration or centrifugation. This solid may be washed with water and if necessary, with an organic solvent like ethanol. The resultant solid may be subjected to air drying and drying under reduced pressure to remove the moisture. The method of the present invention is a method for producing a calcium salt of PQQ by using water as a solvent without any organic solvent.

The white calcium salt of PQQ may coexist with the red calcium salt of PQQ, and can be separated from the red salt through centrifugation. The white salt can be obtained in a crystalline or amorphous form.

The calcium salt of pyrroloquinoline quinone according to the present invention can be obtained in a crystalline form. According to the present invention, there is provided a crystal of a calcium salt of pyrroloquinoline quinone that has a ratio of pyrroloquinoline quinone ions to calcium ions of 1:0.5 to 1.5, and preferably 1:1 to 1.5.

The calcium salt of PQQ according to the present invention can be obtained as a crystal of a calcium salt of pyrroloquinoline quinone, exhibiting, at least, peaks in $2\theta$ at 7.7°, 10.6°, 19.1°, 26.4°, and 38.6° (each within ±0.4°) using Cu Kα radiation as described above. Alternatively, it can be obtained as a crystal of a calcium salt of pyrroloquinoline quinone, exhibiting, at least, peaks in 2θ at 9.8°, 15.3°, 17.1°, 19.7°, 26.3°, and 28.3° (each within ±0.4°). The present calcium salt of PQQ in question is red.

Alternatively, it can be obtained as a crystal of a calcium salt of PQQ, exhibiting, at least, peaks in 2θ at 8.8°, 17.5°, 25.4°, 28.1°, 30.5°, and 33.9° (each within ±0.4°) using Cu Kα radiation as described above. The present calcium salt of PQQ in question is white.

The crystal according to the present invention may be one kind of crystal or a mixture thereof.

The measurement error may be ±0.4°, preferably +0.2°, and more preferably ±0.1°.

The crystalline forms defined in the present invention have only to be reasonably identical in the peak angle since a measurement error is included.

In the present invention, it does not matter even if an alkaline metal remains, as long as the crystalline calcium salt is obtained.

The calcium salt of PQQ according to the present invention is hardly soluble. This hardly soluble calcium salt of PQQ can readily be made soluble by reacting with a chelating substance to remove calcium. Therefore, the composition with a chelating substance is effective in controlling the releasing properties. Any chelating substance that is effective against calcium can be used. Examples of an edible chelating substance include phosphoric acid (sodium hydrogen phosphate, potassium hydrogen phosphate, etc.), pyrophosphoric acid, nucleic acid (DNA sodium etc.), phytic acid, tartaric acid, succinic acid, citric acid, EDTA, hexametaphosphoric acid, and polyphosphoric acid and salts thereof. The amount of such a chelating substance added can be determined depending on its functionality, and may be 0.1 to 1000 times, and more preferably 1 to 100 times the weight of the calcium salt. This method can make the hardly soluble calcium salt soluble in water by reacting with a chelating substance followed by cation exchange of the chelate substance.

The hardly soluble calcium salt of PQQ can release calcium ions and work even when administered as it is to cells or living organisms, since there are many substances in vivo that react with calcium. Also, when the size of the crystas is 1 μm or less that is suitable for cells to take up substances, the hardly soluble crystal may promote the uptake compared to the dissolved state. It is believed that this depends on a mechanism of intracellular uptake, known as endocytosis.

The calcium salt of PQQ according to the present invention can dissolve and simultaneously release calcium ions. The calcium salt of PQQ can readily release calcium ions in the presence of an organic solvent, particularly, dimethyl sulfoxide, dimethylformamide, and dimethylacetamide.

The crystal of the calcium salt of PQQ according to the present invention may be an active ingredient in medicines or functional foods. That is, according to the present invention, there are provided medicines or functional foods comprising a crystal of a calcium salt of PQQ according to the present invention. These medicines or functional foods can be provided in forms such as topical dermatological agents, injections, oral agents and suppositories, or forms such as daily foods and drinks, nutrition-enriched diets and various hospital diets. In addition, the additive used in the preparation may include water, sugars such as fructose and glucose, oils such as peanut oil, soybean oil and olive oil, and glycols such as polyethylene glycol and polypropylene glycol.

Examples of excipients for solid preparations such as tablets, capsules and granules may include sugars such as lactose, sucrose and mannitol, lubricants may include kaolin, talc and magnesium stearate, disintegrants may include starch and sodium alginate, binders may include polyvinyl alcohol, cellulose and gelatin, surfactants may include fatty acid ester, and plasticizers may include glycerin. The examples are not limited by those cited above. Solubility enhancing agents and fillers may be added if necessary.

The crystal of the calcium salt of PQQ may be used alone or in combination with other materials. Examples of the material that may be used in combination include, but not limited thereto, vitamins such as vitamin B complex, vitamin C and vitamin E, amino acids, astaxanthin, carotenoids such as α-carotene and β-carotene, ω-3 fatty acids such as docosahexaenoic acid and eicosapentaenoic acid, and ω-6 fatty acids such as arachidonic acid.

According to a preferred embodiment of the present invention, there are provided a method for producing a calcium salt of pyrroloquinoline quinone, comprising:

(i) mixing an aqueous solution of pyrroloquinoline quinone or an alkali metal salt thereof having a pH of 2.5 to 4 with an aqueous solution of a source of calcium ions; and (ii) obtaining a precipitate from the mixture obtained in the step (i), and a calcium salt of pyrroloquinoline quinone (in the form of crystal) obtained thereby. The calcium salt of pyrroloquinoline quinone thus obtained has a ratio of pyrroloquinoline quinone to calcium ions of about 1:1.

According to a preferred embodiment of the present invention, there are provided a method for producing a calcium salt of pyrroloquinoline quinone, comprising:

(i) mixing an aqueous solution of pyrroloquinoline quinone or an alkali metal salt thereof having a pH of 4.5 to 7 with an aqueous solution of a source of calcium ions; and (ii) obtaining a precipitate from the mixture obtained in the step (i), and a calcium salt of pyrroloquinoline quinone (in the form of crystal) obtained thereby. The calcium salt of pyrroloquinoline quinone thus obtained has a ratio of pyrroloquinoline quinone to calcium ions of about 1:1.5.

According to a preferred embodiment of the present invention, there are provided a method for producing a calcium salt of pyrroloquinoline quinone, comprising:

(i) mixing an aqueous solution of pyrroloquinoline quinone or an alkali metal salt thereof having a pH of 2 to 7 with an aqueous solution of a source of calcium ions;

(ii) obtaining a precipitate from the mixture obtained in the step (i); and (iii) allowing the mixture containing the precipitate obtained in the step (ii) to stand at a pH of 1.5 to 3.5 for 24 hours or more, and a calcium salt of pyrroloquinoline quinone (in the form of crystal) obtained thereby. The calcium salt of pyrroloquinoline quinone thus obtained is white.

According to a preferred embodiment of the present invention, there are provided a method for producing a calcium salt of pyrroloquinoline quinone, comprising (i) mixing an aqueous solution of pyrroloquinoline quinone or an alkali metal salt thereof having a pH of 2 to 7 with an aqueous solution of a source of calcium ions selected from the group consisting of calcium carbonate, calcium chloride, and calcium hydroxide;

(ii) obtaining a precipitate from the mixture obtained in the step (i); and (iii) allowing the mixture containing the precipitate obtained in the step (ii) to stand at a pH of 1.5 to 15 for 24 hours or more, and a calcium salt of pyrroloquinoline quinone (in the form of crystal) obtained thereby. The calcium salt of pyrroloquinoline quinone thus obtained is white.

According to the present invention, the following inventions are further provided.

[1] A calcium salt of pyrroloquinoline quinone, having a ratio of pyrroloquinoline quinone ions to calcium ions of 1:0.5 to 1.5.
[2] A crystal of a calcium salt of pyrroloquinoline quinone, which is exhibiting peaks in 2θ at 7.7°, 10.6°, 19.1°, 26.4°, and 38.6° (each within ±0.4°) in the powder X-ray diffraction using Cu Kα radiation.
[3] A crystal of a calcium salt of pyrroloquinoline quinone, which is exhibiting peaks in 2θ at 9.8°, 15.3°, 17.1°, 19.7°, 26.3°, and 28.3° (each within ±0.4°) in the powder X-ray diffraction using Cu Kα radiation.
[4] A composition comprising a calcium salt of pyrroloquinoline quinone and a chelating substance.
[5] The composition of [4], characterized in that the chelating substance is one or more selected from the group consisting of phosphoric acid, pyrophosphoric acid, nucleic acid, phytic acid, tartaric acid, succinic acid, citric acid, EDTA, hexametaphosphoric acid, and polyphosphoric acid.
[6] A method for producing a calcium salt of pyrroloquinoline quinone, characterized in that an alkali metal salt of pyrroloquinoline quinone is reacted with a calcium compound.

EXAMPLES

The present invention will now be described more specifically with reference to the following examples and comparative examples, but is not intended to be limited thereto.

Analyses for the present invention were performed as follows:
(Powder X-ray Diffraction)
Instrument: RINT 2500 manufactured by RIGAKU
X-ray: Cu/Tube voltage 40 kV/Tube current 100 mA
Divergence slit: 2/3°
Scattering slit: 2/3°
Receiving slit: 0.3 mm
Scanning rate: 4.000°/min
Sampling width: 0.02
(Absorbance Measurement)
Instrument: HITACHI U-2000 (Hitachi)
(ICP Analysis)
Instrument: iCAP6500 (Thermo Scientific)
(NMR Measurement)
Instrument: ECA-500 (JEOL Ltd.)
Analysis conditions:
$^1$H: wPMLG3
$^1$H-$^{13}$C: dipolar hetcor
Rotational frequency: 10 kHz
Probe: Solid 3.2 mm
Sample tube: Silicon nitride
(XPS Analysis)
Instrument: ESCA3400 (SHIMADZU CORPORATION)
Analysis conditions:
X-ray source: Mg Kα
Output: 10 kV 100 W
P.E.: 75
Resolution narrow: high
(CHNO Analysis)
Instrument: EA1112 (Thermo Finnigan)
Analysis conditions:
Combustion temperature: CHN: 950° C.; O: 1060° C.
Column oven temperature: CHN: 65° C.; O: 75° C.
Detector: TCD
Standard substance for calibration curve: antipyrine

Test Example 1

Synthesis of Raw Material

A culture solution obtained by culturing Hyphomicrobium methylovorum DSM1869 was centrifuged, and the bacterial cells were removed to give a culture supernatant containing PQQ, according to Example 1 in Japanese Patent No. 2692167. Here, this bacterial strain is available from DSM (Deutsche Sammlung von Mikroorganismen (German Collection of Microorganisms and Cell Cultures). This culture supernatant was passed through a Sephadex G-10 column (from Pharmacia), on which PQQ was adsorbed. The adsorbed PQQ was eluted with an aqueous NaCl solution to give an aqueous PQQ solution having a pH of 7.5. To the PQQ solution was added NaCl so that the resultant concentration is 60 g/L. The solution was cooled to give a solid. The resultant solid was dissolved in water, and the PQQ had a purity of 99.0% or more as indicated by UV absorption on high performance liquid chromatography. This solid was dissolved in ion-exchanged water to provide 800 g of a solution containing 10 g/L of PQQ. The pH of the solution was adjusted to 3.5 by the addition of hydrochloric acid and then 200 mL of ethanol was added to the solution. At this time, a red solid was precipitated. After being stirred at room temperature for five hours, the solution was allowed to stand at 5° C. for 24 hours, resulting in precipitation of a solid. The solid was recovered through continuous centrifugation, and dried under reduced pressure at 50° C. A powder X-ray diffraction spectrum of the resultant solid was measured. The spectrum of the resultant solid (a disodium salt of PQQ) exhibited few peaks, although a peak was exhibited at the low-angle side, and the resultant solid had low crystallinity.

Example 1

PQQ Crystallization (pH 6.4)

Figure 1:
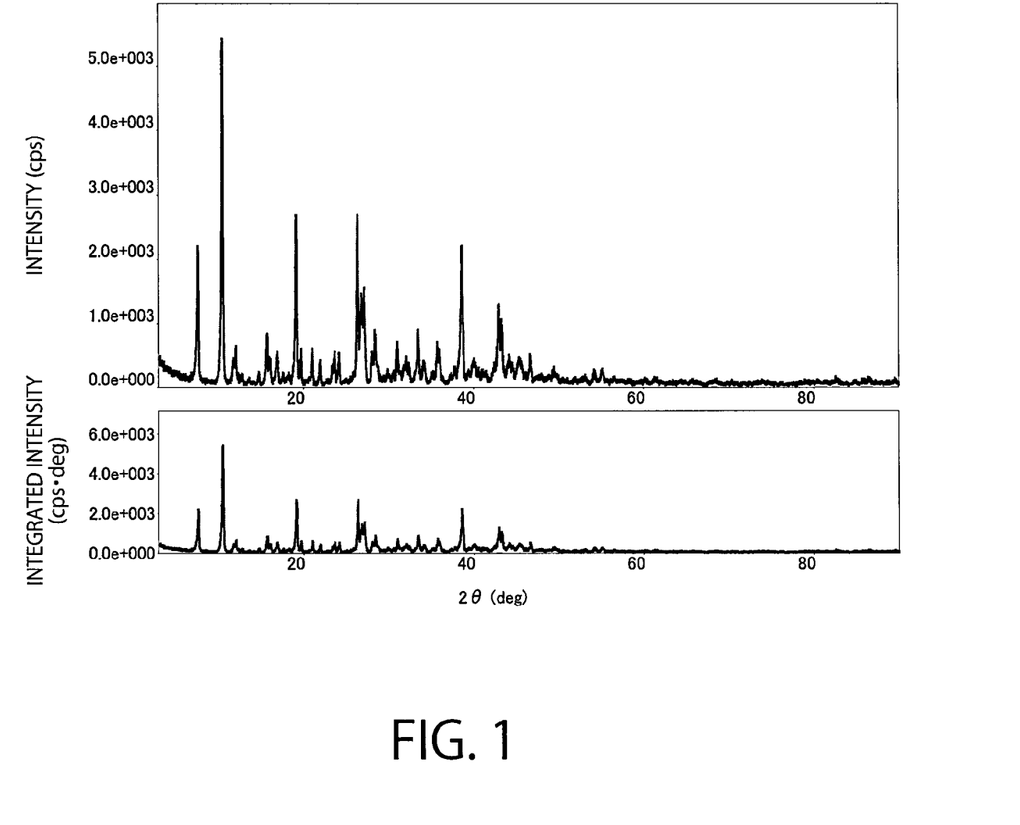
FIG. 1 shows the results obtained by X-ray powder diffraction for Example 1.

The disodium salt of PQQ obtained in Test Example 1 (1 g) was added to water (100 g), and the pH of the mixture was adjusted to 6.4 with NaOH. To the solution was added a solution of calcium chloride (1 g) in water (40 mL). After the mixture was stirred overnight, the precipitated solid was filtered and washed with water and ethanol. This substance was dried at 50° C. under reduced pressure overnight. The deep red crystals recovered weighed 1.18 g. The water content was 23%. The results obtained using ICP analysis indicate that PQQ and Ca were contained in a ratio of 1.5 mol Ca to 1 mol PQQ, and Na content was 0, i.e., sodium was not contained. The results obtained by X-ray powder diffraction for the resultant calcium product is shown in FIG. 1. The resultant calcium product was a crystalline calcium salt of PQQ, exhibiting peaks at 7.7°, 10.6°, 19.1°, 26.4°, and 38.6°. This solid was a crystalline and poorly water-soluble substance.

Example 2

PQQ Crystallization (pH 3.5)

Figure 2:
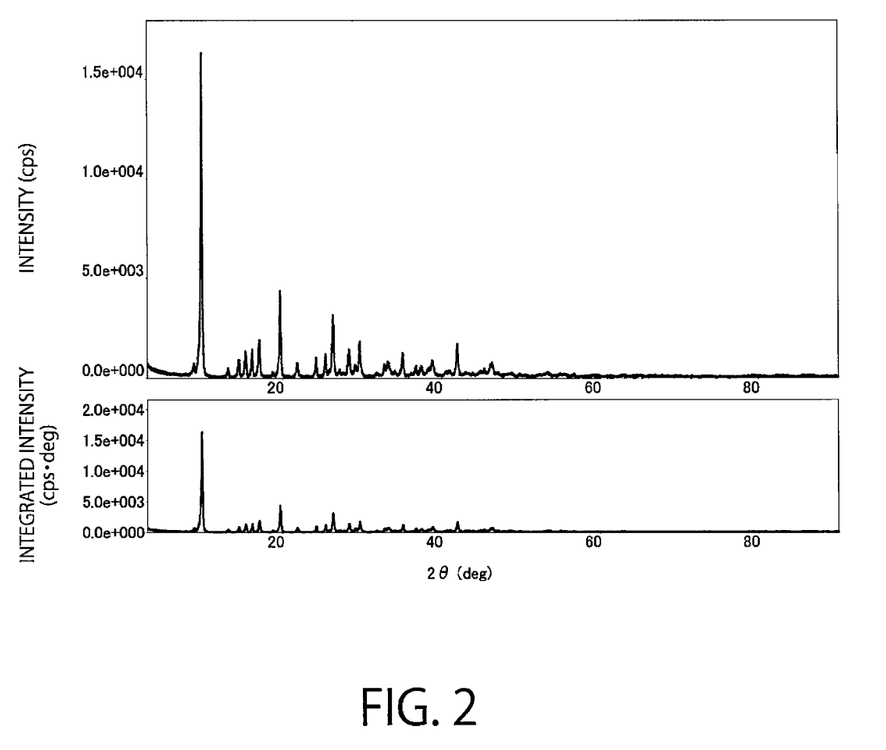
FIG. 2 shows the results obtained by X-ray powder diffraction for Example 2.

The disodium salt of PQQ (3 g) was added to and dissolved in water (800 g). The pH of the solution here was 3.5. To the solution was added a solution of calcium chloride (6 g) in water (100 mL). After the mixture was stirred for two days, the precipitated solid was filtered and washed with water and ethanol. This substance was dried at 70° C. under reduced pressure overnight to give a red solid (3.29 g). The water content was 11%. The results obtained using ICP analysis indicate that PQQ and Ca are contained in a ratio of 1 mol Ca to mol PQQ, and Na content was 0, i.e., sodium was not contained. The results obtained by X-ray powder diffraction for the resultant calcium salt is shown in FIG. 2. The resultant calcium salt was a crystalline calcium salt of PQQ, exhibiting solid was a crystalline and poorly water-soluble substance.

Examples 1-1, 2-1, and Comparative Example 1

Absorption Test Using Cells

PQQ has effects of promoting cell growth and of retarding cell growth at a higher concentration on cultured animal cells. Based on these effects, change in the cell absorption was tested.

Chinese hamster ovary cells (CHO-DHFR⁻, Dainippon Sumitomo Pharma Co., Ltd.) were cultured in a medium (alpha-MEM+10% fetal bovine serum) containing 5% $CO_2$ at 37° C. The cultured cells were added together with 100 µL of the medium to each well of the 96-well plate (IWAKI) so that the cell density per well is 6,000 cells/well, and culture was performed overnight. The culture solution was removed, and the medium having a predetermined test concentration was added thereto. After a 2-day culture, the medium was replaced, a Cell Counting Kit 8 (from DOJINDO LABORATORIES) was used to stain the cells for one hour, and measurement of absorbance was performed at 450 nm. The absorbance in this case is proportional to the cell number.

As the test samples, the crystalline calcium salts of PQQ in Examples 1 and 2 above, and the disodium salt of PQQ or the raw material in Test Example 1, were used for testing after dilution by the medium. The test was duplicated for each sample, and the results were averaged. The test concentration was successively reduced to ½, with 150 µg/mL as the upper limit and 2.3 µg/mL as the lower limit.

The concentration at which the cell count due to PQQ is largest (about 5%) compared to the case without PQQ is recorded as the optimum cell growth concentration. In addition, the concentration at which the total cell count is decreased by about 10% compared to the case without PQQ is recorded as the cell-growth retarding concentration. The results are shown in Table 1 below.

TABLE 1

| | | Optimum cell growth concentration (µg/ML) | Cell growth retarding concentration (µg/ML) |
|---|---|---|---|
| Example 1-1 | PQQCa (pH 6.4) | 2.3 | 75 |
| Example 2-1 | PQQCa (pH 3.5) | 4.7 | 75 |
| Comparative Example 1 | PQQ disodium | 75 | 150 |

It is found that the concentration effective for the cell growth is about one sixteenth to one thirty-second, compared to the case of disodium salt of PQQ, which indicates that absorption is enhanced by the calcium salt. It is found that the cell growth retarding concentration is one-half, which indicates that absorption is enhanced. As described above, it is shown that absorption is enhanced, and that cell permeability is enhanced by the calcium salt of PQQ. In addition, it is indicated that the calcium salt exhibits the influence on cells, and is in the bioavailable form although it is a hardly soluble salt.

Examples 3-10, 1-2, and 2-2

Elution Test

Changes in the solubility of the insoluble salt due to the addition of a chelating substance were measured. The amount of PQQ dissolved was measured by mixing a chelating substance with crystalline calcium salts of PQQ obtained in Examples 1 and 2, adding the mixture to water (1 mL), allowing the reaction mixture to stand for four hours at room temperature, removing insoluble components through centrifugation, and subjecting the resultant liquid to absorption measurement at 450 nm. The results are shown in Table 2.

TABLE 2

| Example | Chelating substance | Calcium salt | Dissolved amount (%) |
|---|---|---|---|
| 3 | $KH_2PO_4$ 0.033 g | PQQCa (pH 3.5) 1.58 mg | 10 |
| 4 | $KH_2PO_4$ 0.030 g | PQQCa (pH 6.4) 1.62 mg | 13 |
| 5 | $Na_2HPO_4$ 0.036 g | PQQCa (pH 3.5) 1.58 mg | 60 |
| 6 | $Na_2HPO_4$ 0.030 g | PQQCa (pH 6.4) 1.62 mg | 64 |
| 7 | $NaH_2PO_4$ 0.067 g | PQQCa (pH 3.5) 1.58 mg | 12 |
| 8 | $NaH_2PO_4$ 0.065 g | PQQCa (pH 6.7) 1.62 mg | 20 |
| 9 | DNA sodium 0.0185 g | PQQCa (pH 3.5) 1.58 mg | 37 |
| 10 | DNA sodium 0.0259 g | PQQCa (pH 6.7) 1.62 mg | 12 |
| 2-2 | none | PQQCa (pH 3.5) 1.58 mg | 3 |
| 1-2 | none | PQQCa (pH 6.4) 1.62 mg | 1 |

As shown in Examples 2-2 and 1-2 in Table 2, the solubility of the calcium salt alone is very low. On the other hand, this insoluble salt can be combined with a chelating substance to enhance the solubility. The solubility can be controlled by changing the substances to be combined, and is varied depending on applications.

Example 11

PQQ Crystallization (pH 4.8)

The experiment was carried out as in Example 1, except that the pH of an aqueous solution of disodium salt of PQQ was adjusted to 4.8. The recovered amount was not different from that in Example 1, and the results obtained by powder X-ray diffraction also showed a crystal structure similar to that in Example 1. This was a salt having a ratio of 1.5 mol Ca to 1 mol PQQ.

Example 12

Crystallization (pH 2.9)

The operations were carried out as in Example 2, except that the pH of an aqueous solution of disodium salt of PQQ was adjusted to 2.9. The recovered amount was similar to Example 2, and the results obtained by powder X-ray diffraction showed a crystalline substance in which crystals obtained in Example 2 (a salt having a PQQ:Ca=1:1) are mixed together with other substances having different crystal structures.

Example 13

PQQ Crystallization (pH 6.6)

A potassium salt of pyrroloquinoline quinone (0.54 g) was dissolved in water (300 mL) and the pH was adjusted to 6.6.

To the solution was added an aqueous solution (20 mL) of calcium chloride (1.4 g), and the resultant solution was stirred overnight. After filtering, the residue was washed with water and ethanol, and dried under reduced pressure to give a solid (0.42 g). The results obtained by powder X-ray diffraction for the resultant substance showed peaks similar to those in Example 1, and a calcium salt having a ratio of 1.5 mol Ca to 1 mol PQQ was produced.

Example 14

Production of White Crystalline Calcium salt of PQQ

Figure 3:
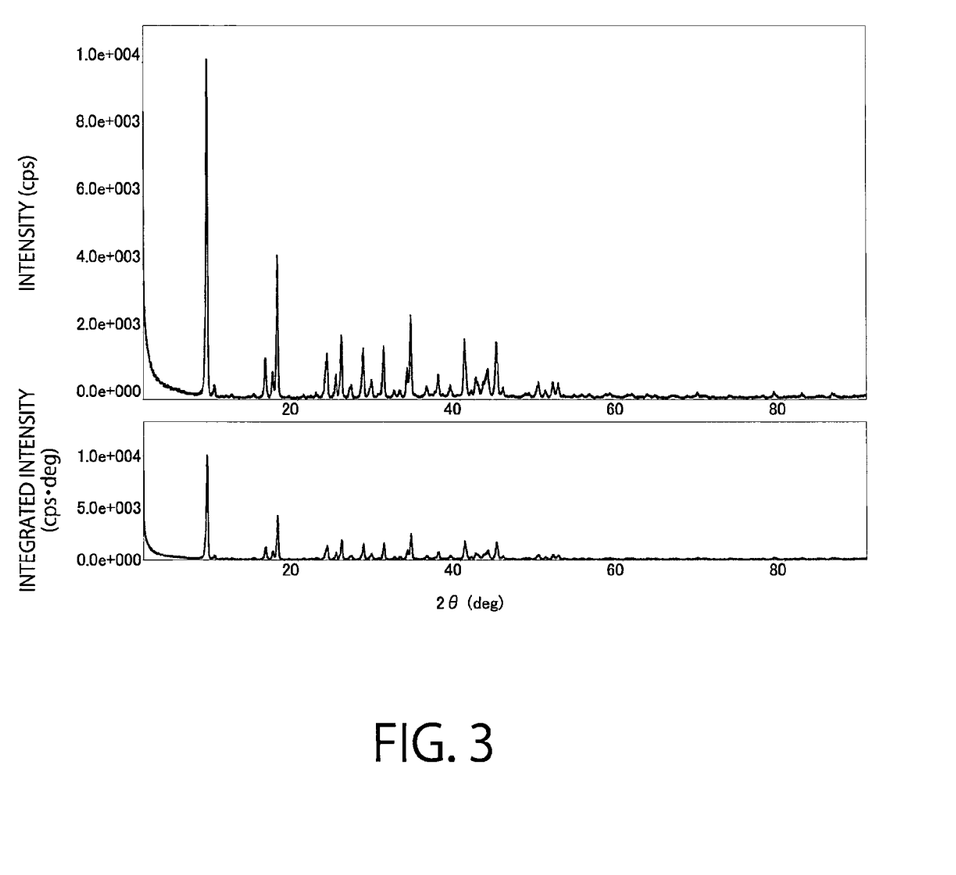
FIG. 3 shows the results obtained by X-ray powder diffraction for Example 14.

The disodium salt of PQQ obtained in Test Example 1 was dissolved in water to prepare an aqueous solution of 2 g/L. To this aqueous solution (400 mL) was added 2 N hydrochloric acid (2 mL). The mixture was mixed with an aqueous solution (170 mL) of calcium chloride (2 g/L) at a temperature of 10° C. The pH during mixing was 2.3. After keeping the mixture at 10° C. for 30 minutes, the reaction mixture was stirred at 40° C. for three days. The reaction mixture was filtered, and the residue was washed with water (50 mL) to give a white solid. The white solid was dried under reduced pressure overnight to give a solid (0.76 g). The results obtained by powder X-ray diffraction are shown in FIG. 3. The resultant solid was a white crystalline substance, exhibiting peaks at 8.8°, 17.5°, 25.4°, 28.1°, 30.5°, and 33.9°.

Example 15

Reaction at 10° C.

The disodium salt of PQQ obtained in Test Example 1 was dissolved in water to prepare an aqueous solution of 2 g/L. To this aqueous solution (400 mL) was added 2 N hydrochloric acid (2 mL). The mixture was mixed with an aqueous solution (170 mL) of calcium chloride (2 g/L) at a temperature of 10° C. The pH during mixing was 2.3. The mixture was allowed to stand at 10° C. for three days. The reaction mixture was filtered, and the residue was washed with water (50 mL) to give a white solid. The white solid was dried under reduced pressure overnight to give a solid (0.78 g). The results obtained by powder X-ray diffraction were the same as those in Example 14.

Example 16

Reaction at pH 2.6

The disodium salt of PQQ obtained in Test Example 1 was dissolved in water to prepare an aqueous solution of 2 g/L. To this aqueous solution (250 mL) was added 2 N hydrochloric acid (0.6 mL). The mixture was mixed with an aqueous solution (120 mL) of calcium chloride (2 g/L) at a temperature of 20° C. The pH during mixing was 2.6. The mixture was stirred at 40° C. for six days. The reaction mixture was filtered, and the residue was washed with ethanol (10 mL) to give a white solid. The white solid was dried under reduced pressure overnight to give a solid (0.50 g). The results obtained by powder X-ray diffraction were the same as those in Example 14.

Example 17

Synthesis of White Crystalline Precursor (a Red Solid)

The experiment was carried out as in Example 15, except that after mixing at 10° C., the mixture was filtered in 30 minutes. As a result, a red solid was obtained. The red solid was dried under reduced pressure overnight to give a red solid (0.79 g).

Example 18 pH Adjustment with Acetic Acid

The disodium salt of PQQ obtained in Test Example 1 was dissolved in water to prepare an aqueous solution of 2 g/L. To this aqueous solution (250 mL) was added acetic acid (4.19 g). The mixture was mixed with aqueous solution (120 mL) of calcium chloride (2 g/L) at room temperature. The pH during mixing was 2.8. The mixture was stirred at 40° C. for six days, and filtered, and the residue was washed with ethanol (10 mL) to give a white solid. The white solid was dried under reduced pressure overnight to give a white solid (0.51 g).

Example 19

Separation of White Solid and Red Solid

The disodium salt of PQQ obtained in Test Example 1 was dissolved in water to prepare an aqueous solution of 2 g/L. To this aqueous solution (400 mL) was added 2 N hydrochloric acid (2 mL). The mixture was mixed with aqueous solution (170 mL) of calcium chloride (2 g/L) at room temperature. The pH during mixing was 2.3. After five minutes, the mixture was allowed to stand at 70° C. for one day. A red solid and a white solid were formed. This mixture was divided into 50 mL centrifuge tubes, the tubes were put in a centrifuge HITACHI himac CF7D2, and centrifugation was performed at 2000 rpm for 30 minutes. At the bottom of the vessels, the solids were precipitated in two layers, the lower red solid and the upper white solid. The white solid and the red solid were divided based on difference in the specific gravity.

Examples 20-22, and Comparative Examples 2-4

Confirmation of Change by pH

An aqueous solution of the disodium salt of PQQ (2 g/L) and an aqueous solution of calcium chloride (2 g/L) were mixed in a 2:1 ratio. The pH was adjusted with hydrochloric acid or NaOH. All samples were red during mixing. The mixture was allowed to stand at 50° C. for three days, and changes in color were observed.

TABLE 3

|  | pH during mixing | pH after adjustment | Change in color |
|---|---|---|---|
| Example 20 | 3.8 | 2.3 | Mixture of white and red |
| Example 21 | 3.5 | 2.0 | white |
| Example 22 | 3.5 | 2.6 | white |
| Comparative Example 2 | 5 | 5 | red |
| Comparative Example 3 | 7 | 7 | brown |
| Comparative Example 4 | 3.5 | 4 | brown |

It is shown that even when the pH was changed after mixing, a white solid was produced. At a pH of 4 or more, a white solid was not produced.

Example 23

Experiment Using Different Raw Materials

The PQQ in the free form was obtained by precipitation after adding hydrochloric acid to an aqueous solution of the disodium salt of PQQ and adjusting the pH of the mixture to 1. An aqueous solution (500 μL) of the PQQ in the free form formed by adding water to the PQQ in the free form obtained as above (3 g/L) and an aqueous solution (750 μL) of calcium carbonate (1 g/L) were mixed and the resultant solution was kept at 70° C. overnight (pH 3.1). A white calcium compound of PQQ was formed.

Examples 24-28

Release of PQQ

The white calcium salt of PQQ (10 mg) produced in Example 15 was added to the respective solvents (2 mL) listed in Table 4. After keeping each resultant mixture at 40° C. for five hours, centrifugation was performed to remove solids, and PQQ was analyzed on high performance liquid chromatography.

TABLE 4

| | Solvent | PQQ recovery (%) | Appearance |
|---|---|---|---|
| Example 24 | Dimethyl sulfoxide | 100 | Red solution |
| Example 25 | $Na_2HPO_4$ 23.5 g/L $NaH_2PO_4$ 5 g/L | 51 | Red solution |
| Example 26 | PBS (GIBCO, pH 7.4) | 4 | Red solid |
| Example 27 | Simulated gastric fluid (KANTO CHEMICAL CO., INC., pH 1.7) | 2 | Red solid |
| Example 28 | Acetic acid 30 mM + Ammonium acetate 70 mM (pH 5) | 7 | White solid |

It is shown that the white calcium salt of PQQ releases calcium ions in an environment rich in DMSO or phosphoric acid ions, and the solution turns red. Also, it is shown that calcium ions are difficult to be released in a simulated gastric fluid, and are easily released in a neutral solution of phosphoric acid. This indicates that the calcium salt of PQQ is a solid that has low reactivity in the stomach, but in intestines where easy absorption occurs, releases calcium ions. Moreover, it is shown that an acetate buffer has little effect in removing added water from a white solid calcium salt of PQQ, and only removes added water from a part of the dissolved salt.

Example 29

Figure 4:
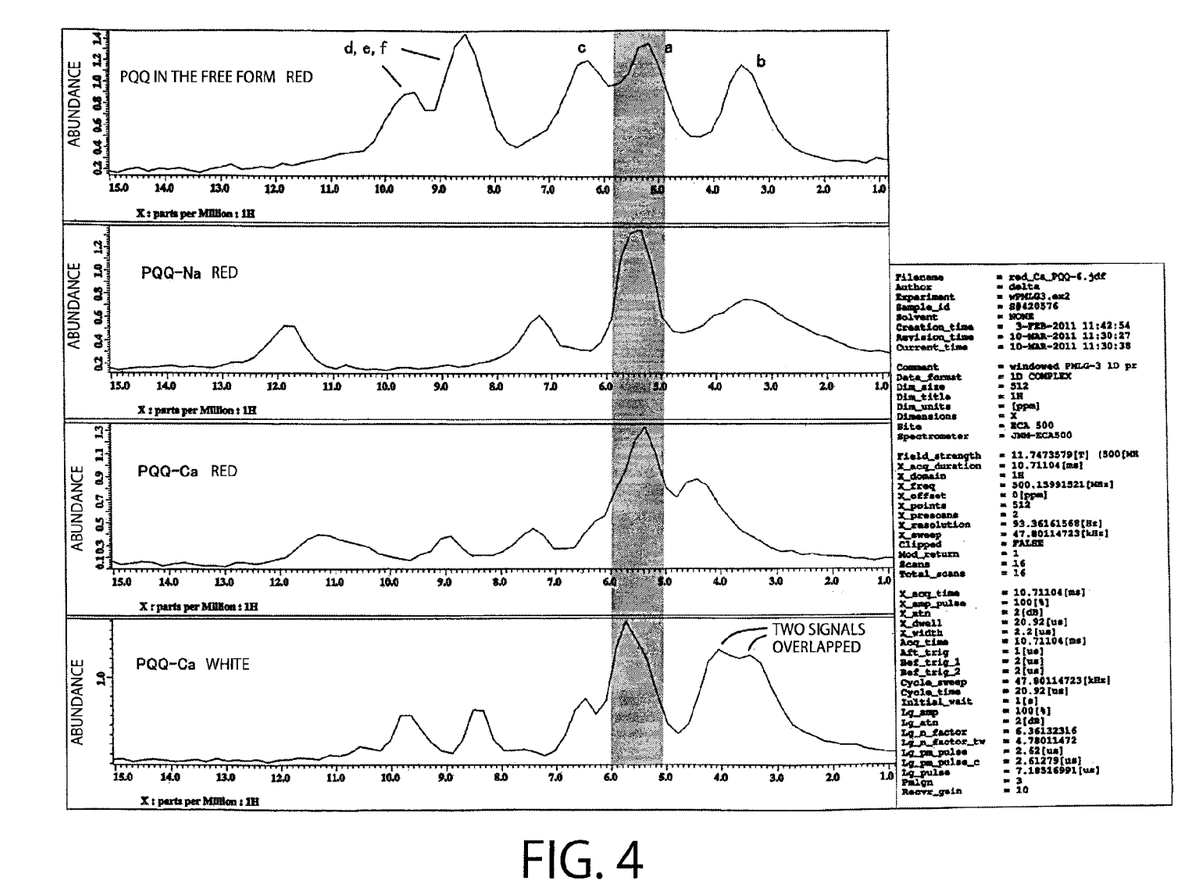
FIG. 4 shows the results obtained from the $^1$H-NMR spectra.

Structural analyses by NMR and XPS were performed for each of the following samples.
1: PQQ in the free form (a red solid PQQ precipitated at pH 1 by adding hydrochloric acid to an aqueous solution of a disodium salt of PQQ)
2: A disodium salt of PQQ (Comparative Example 2)
3: A red calcium compound of PQQ (Example 17)
4: A white calcium compound of PQQ (Example 14)
Solid NMR Measurement In FIG. 4, results of $^1$H-solid NMR (wPMLG3) spectra are shown. For PQQ in the free form, respective signals were assigned based on the chemical shift values. For six protons, only five signals were observed. However, it was estimated that, since there are three COOHs in the structure of PQQ, a signal in the 8 to 9 ppm range is due to two COOH signals. On the other hand, for the red PQQ-Na, the red PQQ-Ca, and the white PQQ-Ca, a signal for H in five-membered-ring (a) was observed in the 5 to 6 ppm range. Moreover, for each sample, a signal estimated to be originated from NH was observed at 5 ppm or less (in the high magnetic field side). However, for the white PQQ-Ca, the signal in the shape of two overlapping signals was observed, which was not observed in other samples.

Figure 5:
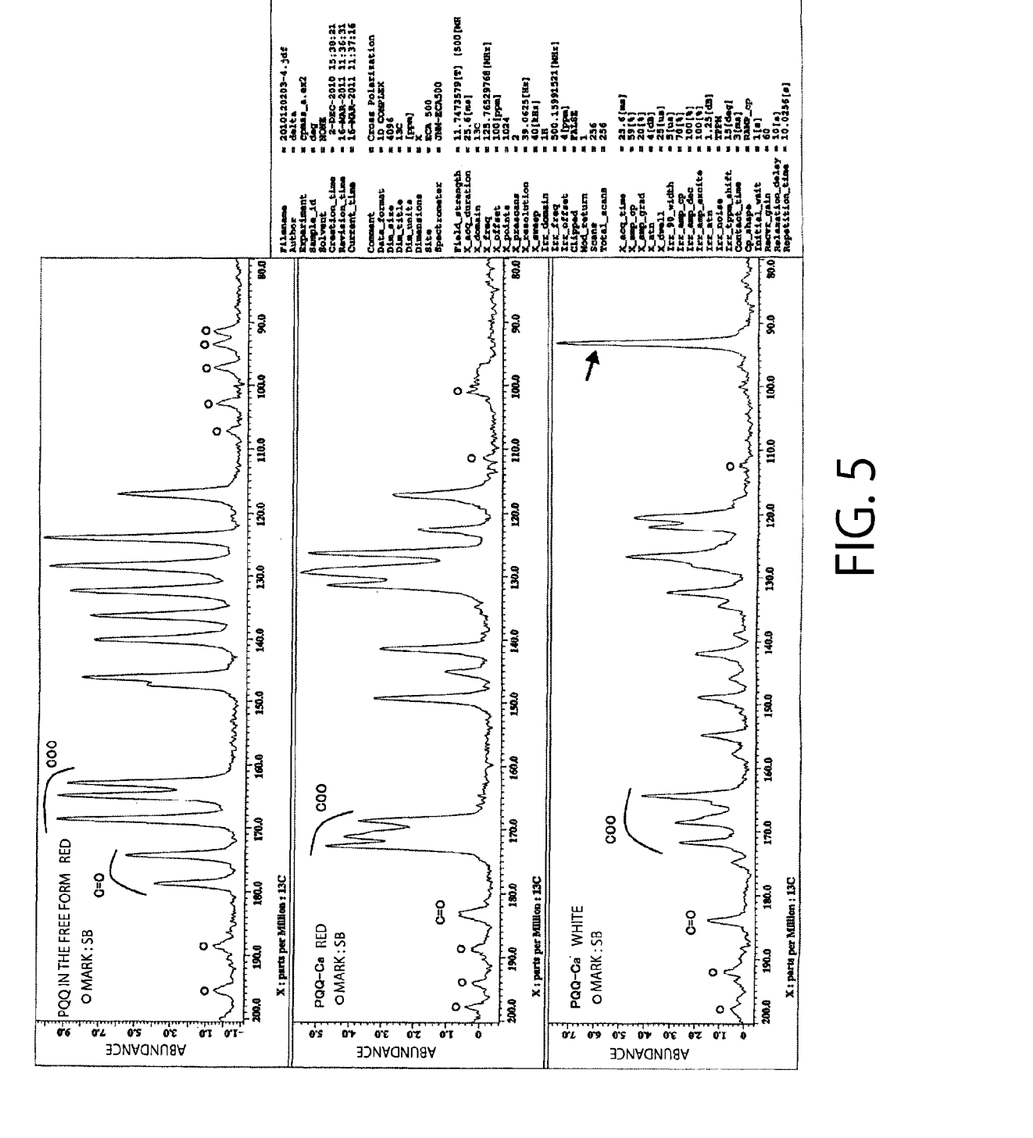
FIG. 5 shows the results obtained from the $^{13}$C-NMR spectra.

In FIG. 5, $^{13}$C-solid NMR (CPMAS) spectra (a 6 mm probe, 9 kHz) are shown. In all of the spectra, it was estimated that signals at 160 ppm or more are originated from COO and C=O, and signals at 160 ppm or less are originated from five-membered and six-membered backbones. Moreover, for the red PQQ-Ca and the white PQQ-Ca, only one signal that was estimated to be originated from C=O was observed. However, it was suggested that the sideband near 190 ppm may be overlapped to hide the signal. For the white PQQ-Ca, a signal near 93 ppm was observed and in 1H measurement, a signal in the 3 to 4 ppm range was observed. Therefore, it is believed that the white PQQ-Ca may have a structure of —CH—O—.

X-Ray Photoelectron Spectroscopy (XPS) Measurement

For determining the change in functional groups, XPS measurement was performed using an ESCA 3400 (SHIMADZU CORPORATION). When the white Ca salt of PQQ was put in the instrument under high vacuum, and was taken out after a period of time, it was found to have turned red (lighter red than the red Ca salt of PQQ). It was estimated that the added water was evaporated under high vacuum, based on the result obtained in the CHNO analysis below. Therefore, the results obtained by XPS analysis for the white Ca salt of PQQ were believed to be obtained in the measurement after the changes in color, and is distinguished with * marks.

Figure 6:
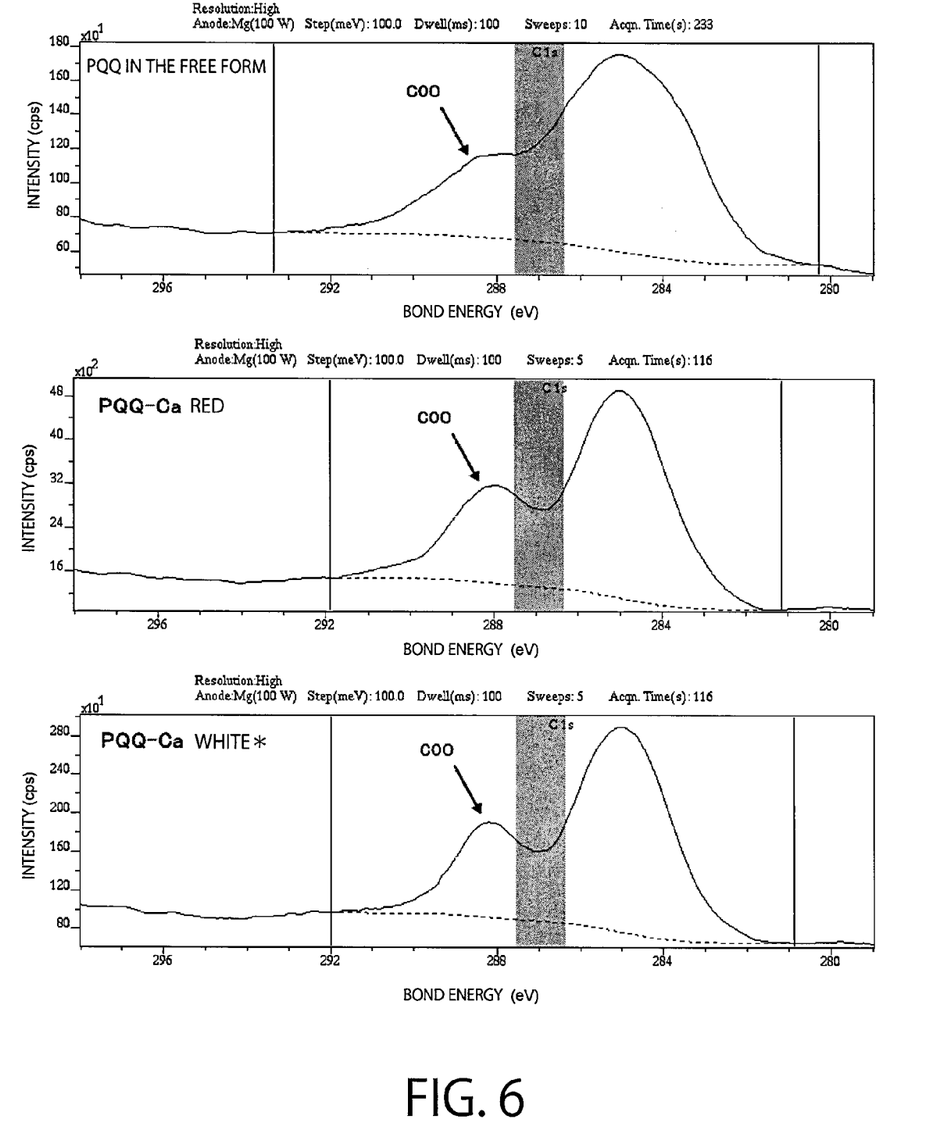
FIG. 6 shows the results obtained through XPS measurements.

In FIG. 6, the measurement results for C1s are shown. In the charge correction, the peak top for C1s at the low energy side was adjusted to 285 eV. Comparing the results in the C1s among PQQ in the free form, the red Ca salt of PQQ, and the white Ca salt of PQQ, a peak originated from COO near 288 to 289 eV was observed for all samples. However, for the red PQQ-Ca and the white PQQ-Ca, there is a dip near 287 eV in both cases, and it was believed that the peak originated from C=O was decreased.

CHNO Analysis

Comparing the red PQQ-Ca with the white PQQ-Ca based on the molar ratio (N=1), there was a difference in H and O, and the composition for the difference corresponded to $H_2O$ (or $H_3O$). Even comparing before and after vacuum pumping (the white PQQ-Ca and the white PQQ-Ca*), there was a difference in H and O, and the composition for the difference corresponded to $H_2O$.

TABLE 5

| | C | H | N | O | Other |
|---|---|---|---|---|---|
| Red PQQ-Ca | 41.8 | 1.7 | 6.7 | 34.1 | 15.7 |
| White PQQ-Ca | 39.2 | 2.4 | 6.3 | 36.4 | 15.7 |
| White PQQ-Ca* | 42.5 | 1.8 | 6.7 | 33.5 | 15.5 |

Summarizing these results, it is believed that one quinine moiety has undergone a structural change to have CH—OH, resulting in a hydrated structure. From the elemental analysis for PQQ, one PQQ is considered to have one calcium atom and about two water molecules. It is considered that the presence of calcium ions provides hydration of PQQ, which inhibits the extension of the conjugate form, resulting in color change to white. This hydrated structure can easily be changed, and returned to the original structure.

The invention claimed is:

1. A crystal of a calcium salt of pyrroloquinoline quinone, having peaks in 2θ at 7.7°, 10.6°, 19.1°, 26.4°, and 38.6° (each within ±0.4°) in powder X-ray diffraction using Cu Kα radiation, wherein the calcium salt of pyrroloquinoline quinone has a ratio of pyrroloquinoline quinone to calcium ions of about 1:1.5.

2. A crystal of a calcium salt of pyrroloquinoline quinone, having peaks in 2θ at 9.8°, 15.3°, 17.1°, 19.7°, 26.3°, and 28.3° (each within ±0.4°) in powder X-ray diffraction using Cu Kα radiation, wherein the calcium salt of pyrroloquinoline quinone has a ratio of pyrroloquinoline quinone to calcium ions of about 1:1.

3. A crystal of a calcium salt of pyrroloquinoline quinone, having peaks in 2θ at 8.8°, 17.5°, 25.4°, 28.1°, 30.5°, and 33.9° (each within ±0.4°) in powder X-ray diffraction using Cu Kα radiation, wherein the calcium salt of pyrroloquinoline quinone has a ratio of pyrroloquinoline quinone to calcium ions of about 1:1.

4. A method of preparing a pyrroloquinoline quinone-containing composition comprising reacting the crystal of the calcium salt of pyrroloquinoline quinone according to claim 1 with a chelating substance.

5. The crystal of the calcium salt of pyrroloquinoline quinone according to claim 2, which has a red color.

6. The crystal of the calcium salt of pyrroloquinoline quinone according to claim 3, which has a white color.

* * * * *